United States Patent [19]

Rodomista et al.

[11] Patent Number: 4,991,451
[45] Date of Patent: Feb. 12, 1991

[54] PROBE WIPING

[75] Inventors: Guy F. Rodomista, Natick; Michael J. Monahan, Needham, both of Mass.

[73] Assignee: Nova Biomedical Corporation, Waltham, Mass.

[21] Appl. No.: 370,405

[22] Filed: Jun. 22, 1989

[51] Int. Cl.⁵ .............................................. B01L 3/02
[52] U.S. Cl. ................................................. 73/864.24
[58] Field of Search ........................ 73/864.11–864.15, 73/864.21–864.25, 866.5; 422/100, 63–65, 67; 134/104.1, 166 R, 166 C, 168 R, 168 C, 170; 15/97 R, 101, 104.04

[56] References Cited

U.S. PATENT DOCUMENTS

| | | | |
|---|---|---|---|
| 2,850,754 | 9/1958 | Davis | 15/104.04 |
| 3,188,181 | 6/1965 | Peterson et al. | 23/259 |
| 3,666,420 | 5/1972 | Paatzsch | 23/253 |
| 3,875,407 | 4/1975 | Hayne | 250/324 |
| 4,094,196 | 6/1978 | Friswell | 73/864.21 |
| 4,457,184 | 7/1984 | Shiono | 73/864 |
| 4,487,081 | 12/1984 | De Vaughn et al. | 73/864.16 |
| 4,499,053 | 2/1985 | Jones | 73/864.25 |

Primary Examiner—Robert Raevis

[57] ABSTRACT

Apparatus for removing fluid residue from an outer surface of a probe after it has been exposed to a fluid sample; the apparatus includes a wiper having a contact surface for wiping the residue from the outer surface of the probe, and a fluid flow path that cooperates with the contact surface for withdrawing wiped residue away from the contact surface and the probe; and a mechanism is provided for causing the contact surface to be swept along the outer surface of the probe. An apparatus for cleaning the outer surface of a probe after it is exposed to a fluid sample including a wiper for contacting the outer surface of the probe and a mechanism for causing relative motion between the wiper and the probe to wipe fluid from the outer surface.

18 Claims, 2 Drawing Sheets

PROBE WIPING

BACKGROUND OF THE INVENTION

This invention relates to cleaning probes that touch fluids.

In a chemical analyzer, for example, liquid from an earlier sample may remain on the outside surface of such a probe, thus contaminating the next liquid sample into which the probe is inserted. It is known to clean the probe between samples by immersing it in a wash, or by blowing off the liquid, or by ultrasonic cleaning.

SUMMARY OF THE INVENTION

In general, the invention features apparatus for removing fluid residue from an outer surface of a probe after it has been exposed to a fluid sample; the apparatus includes a wiper having a contact surface for wiping the residue from the outer surface of the probe, and a fluid flow path that cooperates with the contact surface for withdrawing wiped residue away from the contact surface and the probe; and a mechanism is provided for causing the contact surface to be swept along the outer surface of the probe.

Preferred embodiments include the following features. The fluid flow path and the contact surface are an integral mass of a wicking material (preferably felt). The wiper is disk shaped with a central aperture to receive the probe. The flow path extends radially from the probe. The wiper includes an evaporation surface at the lateral periphery of the wiper and exposed to the ambient. A reservoir is provided for receiving and temporarily storing fluid from the wiper. The reservoir is in contact with the wiper at a surface which allows passage of the fluid between the wiper and the reservoir. The outer lateral peripheral surface of the reservoir is enclosed by a fluid impermeable wall. The reservoir is a tube, e.g. cylinder, of wicking material (felt) having an inner cylindrical wall surface whose diameter is larger than the probe; the reservoir is not in direct contact with the outer surface of the probe. The wiper is surrounded by a housing having a vent to permit evaporation of fluid from the wiper.

The probe is thus kept free of contaminating fluid. The wiper is inexpensive, easily made and installed, easily replaced, and highly effective. The reservoir assures a substantial capacity for wiped fluid even when the frequency of probe wiping is sometimes high.

Other advantages and features will become apparent from the following description of the preferred embodiments and from the claims.

DESCRIPTION OF THE PREFERRED EMBODIMENT

The drawings are first briefly described.

DRAWINGS

STRUCTURE

Figure 1:
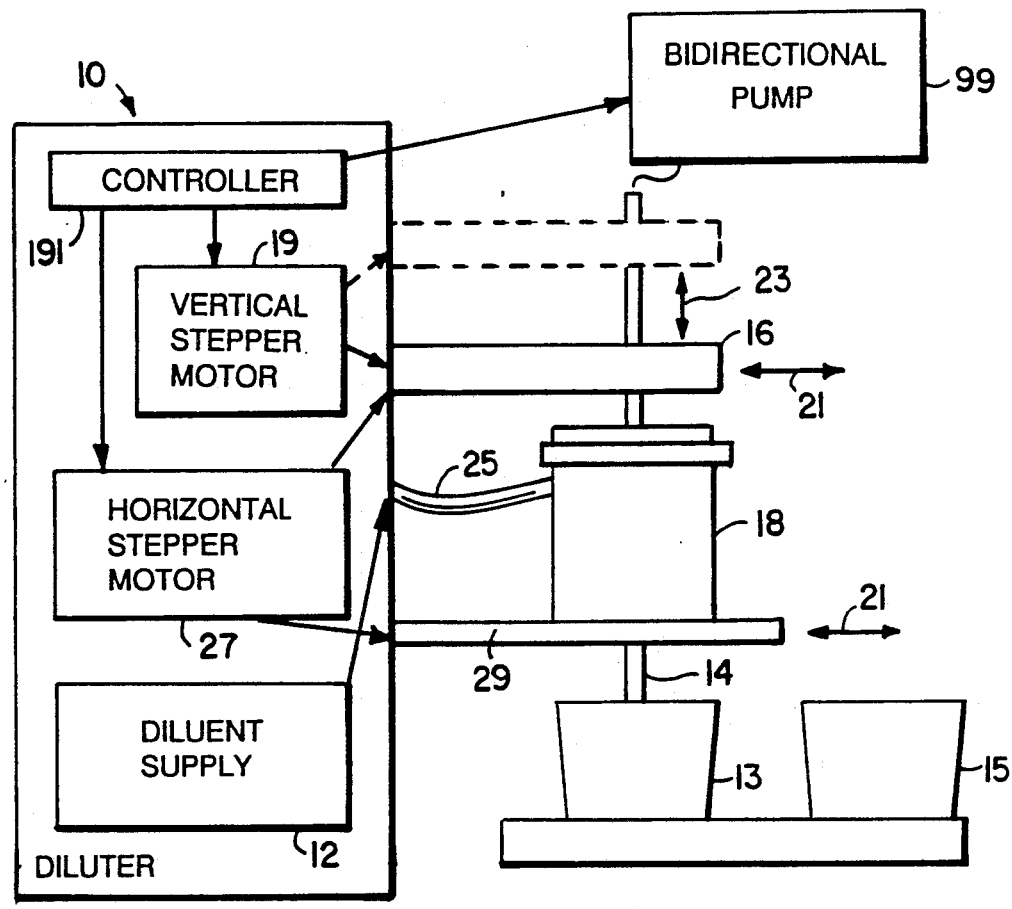
FIG. 1 is a schematic diagram of a fluid sample diluter with probe wiper.

Referring to FIG. 1, a sample diluter 10 is arranged to draw a sample of, e.g., blood, from a sample cup 13, dilute the sample, and then deposit the diluted sample into a second sample cup 15. The sample is drawn from cup 13 and the diluted sample is returned to cup 15 through a hollow stainless steel probe 14 which is supported from above by an arm 16 and passes through a wipe assembly 18. In order to raise and lower the probe for drawing the sample and depositing the diluted sample, arm 16 may be moved up and down (arrows 23) relative to the diluter 10 by a stepper motor 19 in response to commands from a controller 191. A second supporting arm 29 supports assembly 18 and is held in a vertically fixed position so that when the probe is raised and lowered by arm 16, the probe moves up and down relative to the wipe assembly.

Arms 16 and 29 are mechanically linked for horizontal motion in order to move the probe to appropriate positions for serving both cups 13 and 15. A second stepper motor 27 (also commanded by controller 191) drives arms 16 and 29 left and right (arrows 21).

Wipe assembly 18 is connected to a supply of diluent 12 via a flexible tube 25

Figure 3:
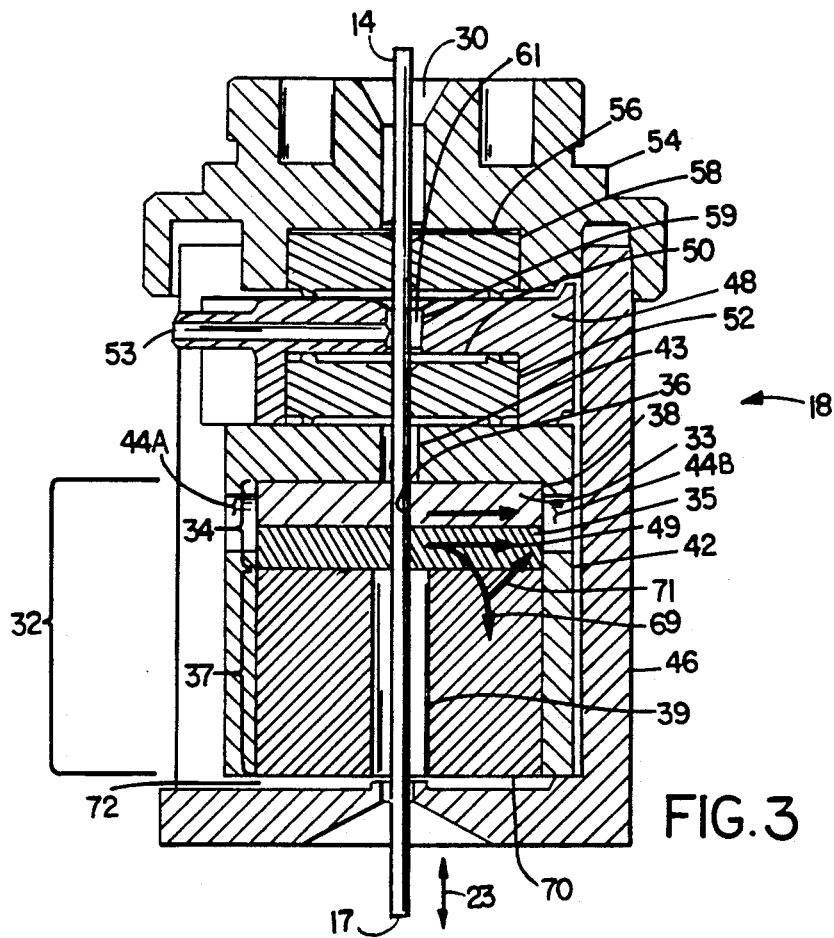
FIG. 3 is a side sectional view of the FIG. 2 wipe assembly.
Figure 2:
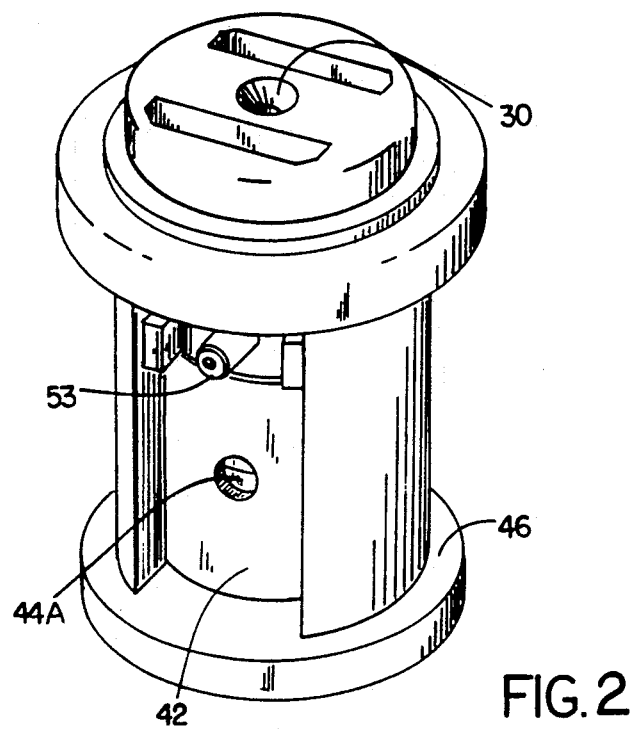
FIG. 2 is a perspective view of the wipe assembly of the FIG. 1 sample diluter.

Referring to FIGS. 2 and 3, probe 14 is housed in a central passage 30 extending from the top end to the bottom end of wipe assembly 18. Passage 30 is defined by central apertures in a series of elements arranged from the top to the bottom of assembly 18. The elements include a disk shaped wiper 34 that is in direct contact with the outer surface of the probe. Disk-shaped wiper 34 includes two identical needled polyester felt (with scrim reinforcement) disks 33, 35, each having a central aperture slightly smaller in diameter than the outer surface of the probe, thus providing a wiping (contact) surface 36 in contact with the probe. The outer peripheral surface 38 of wiper 34 provides an evaporation surface that permits fluid to evaporate to the air. Fluid wiped from the probe is wicked away to the peripheral surface 38 via the felt of the wiper. Thus the wiper provides a fluid flow path in the direction of arrow 49 that enables the fluid to be drawn away from the contact surface and the probe.

Immediately below wiper 34 is a tubular, e.g. cylindrical shaped reservoir element 37 (also made or needled polyester felt available from Tex-Tech Industries, No. Monmouth Me). Reservoir 37 has the same outer diameter as wiper 34 but has a larger tubular, e.g., cylindrical, central aperture 39 that is not in contact with the probe, the contact surface 36 of the wiper and aperture 39 being coaxial. The bottom surface of wiper 34 is in contact with the top surface of reservoir 37 so that fluid that is wiped from the probe can be wicked into the reservoir as indicated by arrow 69 and also wicked back into the wiper toward the evaporation surface as indicated by arrow 71.

Wiper 34 is held in a wiper cartridge 42 which has vents 44A, 44B adjacent to the peripheral surface 38 of wiper 34; the vents expose the outer evaporation surface of the wiper to the ambient air. The upper surface of wiper cartridge 42 has a clearance hole 43, and the lower surface rests on the bottom wall of a housing 46. The reservoir's outer lateral peripheral surface is completely covered by the fluid impervious cartridge wall so that no operator exposure to contaminants can occur directly from the reservoir. The housing 46 includes a gap 72 forming a vent between the housing and the lower surface of the wiper cartridge 42 which allows evaporation of fluid residue from the outer lower peripheral surface 70 of the reservoir.

Lying above the wiper cartridge within housing 46 is a clear module 48 having a recess 50 in which a rubber septum 52 is held. A central clearance hole 50 opens into a radial passage 53. Tube 25 (FIG. 1) is attached over the exposed end of passage 53. Septum 52 seals tightly around the outside surface of the probe thus forming the bottom wall of a small chamber 61 whose upper wall is formed by a second rubber septum 58. Septum 58 is held in a recess 56 of a clear lid 54 which is attached to housing 46.

The upper end of probe 14 is connected to a bidirectional pumping mechanism 99 (FIG. 1) to enable fluid to be drawn into and expelled from the probe.

OPERATION

In operation, prior to diluting a sample in cup 13, probe 14 is withdrawn by stepper motor 19 so that the tip of the probe is within chamber 61; the bidirectional pump is activated to draw an appropriate volume of diluent from the diluent supply 12 through tube 25 into the probe. Next stepper motor 27 positions the probe above cup 13 and stepper motor 19 lowers the probe into the sample. Bidirectional pump 99 then withdraws a volume of the sample into probe 14. Stepper motor 19 then withdraws probe 14 from the cup. As the probe is withdrawn so that its tip is in the chamber defined within opening 43, wiper 34 cleans sample solution from the outside surface of probe 14. The wiped fluid then is wicked away toward evaporation surface 38 and into reservoir 37. Fluid reaching surface 38 evaporates through 44A, 44B. Any excess fluid is wicked into the reservoir for temporary storage. As wiper 34 dries, fluid held in reservoir 37 eventually wicks back through wiper 34 to surface 38, where it evaporates.

After the sample is withdrawn from cup 13, motor 27 then repositions the probe over cup 15. Probe 14 is lowered so that its tip is clear of the bottom of arm 29 and lies just below lip of the cup. The sample, followed by the dilutent, is then expelled into cup 15 where the turbulence generated by the expulsion mixes the sample volume with the diluent. Then the probe tip is withdrawn into chamber 61 (being wiped clean as it is withdrawn) and recharged with diluent ready for the next sample.

What is claimed is:

1. Apparatus for removing fluid residue from an outer surface of a probe after said probe has been exposed to a fluid sample, comprising
   a wiper comprising wicking material having a contact surface for wiping the residue from the outer surface of the probe, a fluid flow path cooperating with the contact surface for withdrawing wiped residue away from the contact surface and the probe, and an evaporation surface, along said flow path, exposed to air at the outer periphery thereof for evaporating fluid residue passing thereto,
   a reservoir, separate from the wiper, comprising a tube of wicking material having one peripheral surface in contact with the wiper for receiving fluid residue from the wiper, for temporarily storing fluid residue, and for allowing passage of fluid residue between the reservoir and the wiper, said reservoir having a tubular central aperture, said wiper being positioned at one end of said tubular aperture with the contact surface of the wiper coaxial therewith and the other end of said tubular aperture being open, said tubular aperture having a larger lateral dimension than the diameter of said outer surface of said probe, such that said reservoir is not in direct contact with said outer surface of said probe, and
   a mechanism for causing the contact surface to be swept along the outer surface of the probe.

2. The apparatus of claim 1 wherein the fluid flow path comprises a wicking material.

3. The apparatus of claim 2 wherein the fluid flow path comprises felt.

4. The apparatus of claim 1 wherein the contact surface comprises a wicking material.

5. The apparatus of claim 4 wherein the contact surface comprises felt.

6. The apparatus of claim 1 wherein said contact surface and said fluid flow path comprise an integral mass of wicking material.

7. The apparatus of claim 1 wherein said probe is cylindrical and said wiper is disk shaped with a central aperture to receive the probe.

8. The apparatus of claim 7 wherein the flow path extends radially from the probe.

9. The apparatus of claim 1 wherein said wiper is surrounded by a housing having a vent at the lateral periphery of said wiper to permit evaporation of said fluid residue from said evaporation surface of said wiper.

10. The apparatus of claim 9 wherein said reservoir is disposed underneath said wiper.

11. The apparatus of claim 10 wherein the outer lateral peripheral surface of said reservoir is enclosed by a fluid impermeable wall that prevents evaporation of said fluid residue from said outer lateral peripheral surface.

12. The apparatus of claim 11 wherein said reservoir is surrounded by a housing having a vent at the outer lower periphery of said reservoir to permit evaporation of said fluid residue from the outer lower peripheral surface of said reservoir.

13. The apparatus of claim 1 wherein the outer lateral peripheral surface of said reservoir is enclosed by a fluid impermeable wall that prevents evaporation of said fluid residue from said outer lateral peripheral surface of said reservoir.

14. The apparatus of claim 1 wherein said reservoir is disposed underneath said wiper.

15. The apparatus of claim 1 wherein the evaporation surface is exposed to the ambient.

16. The apparatus of claim 1 wherein said contact surface, said fluid flow path, and said evaporation surface of said wiper comprise an integral mass of wicking material.

17. The apparatus of claim 16 wherein said reservoir tubular central aperture comprises an inner cylindrical wall surface whose diameter is larger than the diameter of said probe.

18. The apparatus of claim 16 wherein said wicking material comprises felt.

* * * * *